US006599884B2

(12) United States Patent
Avrutov et al.

(10) Patent No.: US 6,599,884 B2
(45) Date of Patent: Jul. 29, 2003

(54) PROCESSES FOR PREPARING CLARITHROMYCIN POLYMORPHS AND NOVEL POLYMORPH IV

(75) Inventors: Ilya Avrutov, Bat Hefer (IL); Igor Lifshitz, Petach Tikva (IL); Ronen Borochovitz, Netanya (IL); Basem Masarwa, Taibe (IL); Edi Schwartz, Rechovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 09/736,449

(22) Filed: Dec. 15, 2000

(65) Prior Publication Data

US 2002/0026038 A1 Feb. 28, 2002

Related U.S. Application Data

(60) Provisional application No. 60/171,221, filed on Dec. 16, 1999, and provisional application No. 60/171,839, filed on Dec. 22, 1999.

(51) Int. Cl.$^7$ .............................................. A61K 31/70
(52) U.S. Cl. .......................................... 514/29; 536/7.2
(58) Field of Search ............................ 536/7.2, 7.5, 29

(56) References Cited

U.S. PATENT DOCUMENTS

| | | | |
|---|---|---|---|
| 4,331,803 A | 5/1982 | Watanabe et al. | |
| 4,349,545 A | 9/1982 | D'Ambrieres et al. | |
| 4,640,910 A | 2/1987 | Faubl et al. | |
| 4,670,549 A | 6/1987 | Morimoto et al. | |
| 4,672,056 A | 6/1987 | Fernandes et al. | 514/29 |
| 4,672,109 A | 6/1987 | Watanabe et al. | |
| 4,680,386 A | 7/1987 | Morimoto et al. | |
| 4,957,905 A | 9/1990 | Hunt | |
| 4,990,602 A | 2/1991 | Morimoto et al. | |
| 5,274,085 A | 12/1993 | Amano et al. | |
| 5,719,272 A | 2/1998 | Yang et al. | |
| 5,756,473 A | 5/1998 | Liu et al. | |
| 5,808,017 A | 9/1998 | Chang | |
| 5,837,829 A | 11/1998 | Ku | |
| 5,844,105 A | 12/1998 | Liu et al. | |
| 5,852,180 A | 12/1998 | Patel | |
| 5,858,986 A | 1/1999 | Liu et al. | |
| 5,864,023 A | 1/1999 | Ku et al. | |
| 5,872,229 A | 2/1999 | Liu et al. | |
| 5,892,008 A | 4/1999 | Ku et al. | |
| 5,932,710 A | 8/1999 | Liu et al. | |
| 5,945,405 A | 8/1999 | Spanton et al. | |
| 6,506,886 B1 | 1/2003 | Lee et al. | |

FOREIGN PATENT DOCUMENTS

| | | |
|---|---|---|
| CA | 1 225 637 | 8/1987 |
| EP | 0 158 467 B1 | 10/1985 |
| EP | 0 158 467 A2 | 10/1985 |
| EP | 0 180 415 B1 | 5/1986 |
| EP | 0 180 415 A2 | 5/1986 |
| EP | 0 272 110 B1 | 6/1988 |
| EP | 0 272 110 A3 | 6/1988 |
| WO | 98/04574 | 2/1998 |
| WO | 98/31699 | 7/1998 |
| WO | 00/14099 | 3/2000 |

Primary Examiner—Elli Peselev
(74) Attorney, Agent, or Firm—Kenyon & Kenyon

(57) ABSTRACT

The present invention relates to processes for converting clarithromycin Form 0 to clarithromycin Form II, which include slurrying clarithromycin the Form 0 in water. The present invention also relates to processes for the preparation of clarithromycin Form II by converting erythromycin A to clarithromycin and thereafter converting clarithromycin Form 0 to clarithromycin Form II by slurrying. The present invention further relates to the novel clarithromycin polymorph Form IV, a process for its preparation, pharmaceutical compositions comprising the compound, and methods of using the compound as a therapeutic agent.

40 Claims, 1 Drawing Sheet

PROCESSES FOR PREPARING CLARITHROMYCIN POLYMORPHS AND NOVEL POLYMORPH IV

CROSS REFERENCE TO RELATED APPLICATION

The present application claims the benefit of U.S. Provisional Application Nos. 60/171,839 filed on Dec. 22, 1999 and 60/171,221 filed on Dec. 16, 1999.

FIELD OF THE INVENTION

The invention relates to methods for making polymorphic Form II of clarithromycin via slurrying polymorphic Form 0 of clarithromycin in water. The invention also relates to methods for making polymorphic Form IV of clarithromycin.

By slurrying in water, clarithromycin Form 0 can be converted to clarithromycin Form II. Under different conditions, a novel polymorphic form of clarithromycin, designated Form IV can be formed. The invention relates to the use of clarithromycin polymorphs so formed in pharmaceutical compositions; and to methods of using them.

BACKGROUND OF THE INVENTION

6-O-methyl erythromycin A (clarithromycin) is a semi-synthetic macrolide antibiotic related to erythromycin A. Clarithromycin exhibits excellent antibacterial activity against gram-positive bacteria, some gram-negative bacteria, anaerobic bacteria, Mycoplasma, and Chlamydia. It is stable under acidic conditions and is efficacious when administered orally. Clarithromycin is useful therapy for infections of the upper respiratory tract in children and adults. Clarithromycin is stable under acidic conditions and is efficacious when administered orally.

The chemical structure of clarithromycin is:

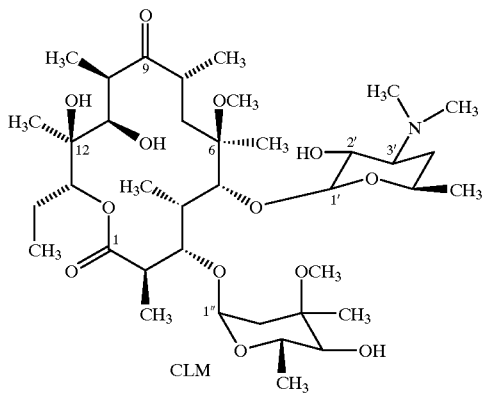

-continued

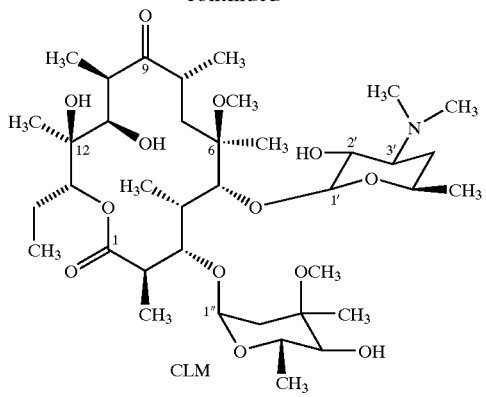

CLM

Several crystal forms of clarithromycin and/or solvates of clarithromycin, "Form 0," "Form I", and "Form II" have been identified as indicated in U.S. Pat. No. 5,945,405. The crystal form of clarithromycin is typically identified by the powder x-ray diffraction patterns. Different crystalline forms of clarithromycin may have different thermal stability, cost of preparation, dissolution characteristics and bioavailability.

Various methods of preparing clarithromycin described in the patent literature have been reported to result in different forms of clarithromycin. Purification of crude clarithromycin has been reported to convert one form of clarithromycin to another form. For example, methods in which the compound is purified by recrystallization from ethanol, have been reported to result in the initial formation of Form 0 solvate (see U.S. Pat. No. 5,945,405) or in the initial formation of Form I (See U.S. Pat. No. 5,858,986). The Form 0 solvate may be used as a therapeutic agent, as described in U.S. Pat. No. 5,945,405. The '405 patent discloses that the Form 0 solvate may be converted to the non-solvated Form I by removing the solvent by drying at a temperature of from about 0° C. to about 50° C. Another form, Form II, is reported to be relatively thermodynamically stable compared to Form I. The clarithromycin currently marketed in the United States under the trademark Biaxin® is formulated using Form II.

Several methods of converting clarithromycin Form 0 or Form I to Form II have been described. One such method, as described in U.S. Pat. No. 4,945,405 and U.S. Pat. No. 5,858,986, is to heat Form 0 under vacuum at a temperature of between about 70° C. and 110° C. According to this patent, the Form 0 solvate first converts to Form I clarithromycin and then to Form II. This method is described in U.S. Pat. No. 4,945,405 and U.S. Pat. No. 5,858,986. However, this vacuum drying step of converting Form 0 to Form II is expensive in both energy and material handling. Clarithromycin Form II has been reported to be formed when Form I is crystallized from various solvents, including ethanol and water (U.S. Pat. No. 5,844,105).

SUMMARY OF THE INVENTION

The invention relates to methods for making polymorphic forms of clarithromycin via slurrying clarithromycin Form 0 in water. By slurrying in water, clarithromycin Form 0 can be converted to clarithromycin Form II.

Under different conditions, a novel polymorphic form of clarithromycin, designated Form IV, can be formed. Such conditions for example, include precipitation from aqueous ethanol at neutralization of the salt of clarithromycin with formic acid by sodium hydroxide at low temperature.

The invention relates to the use of clarithromycin polymorphs so formed in pharmaceutical compositions; and to methods of using them.

The present invention relates to a process for converting clarithromycin Form 0 to clarithromycin Form II, which includes slurrying clarithromycin Form 0 in water. The present invention also relates to processes for the preparation of clarithromycin Form II by converting erythromycin A to clarithromycin and thereafter, converting clarithromycin Form 0 to clarithromycin Form II by slurrying.

Additionally, the present invention relates to a novel polymorph of clarithromycin, that is, clarithromycin Form IV, a process for its preparation, pharmaceutical compositions that include Form IV and methods of using Form IV as a therapeutic agent.

Clarithromycin Form IV can be characterized by its powder x-ray diffraction pattern, which exhibits characteristic peaks at 7.6°±0.2, 8.1°±0.2, 9.40°±0.2, 11.0°±0.2, 12.0°±0.2, 15.4°±0.2, 16.5°±0.2, 18.7°±0.2, and 19.3°±0.2.

DETAILED DESCRIPTION OF THE INVENTION

Figure 1:
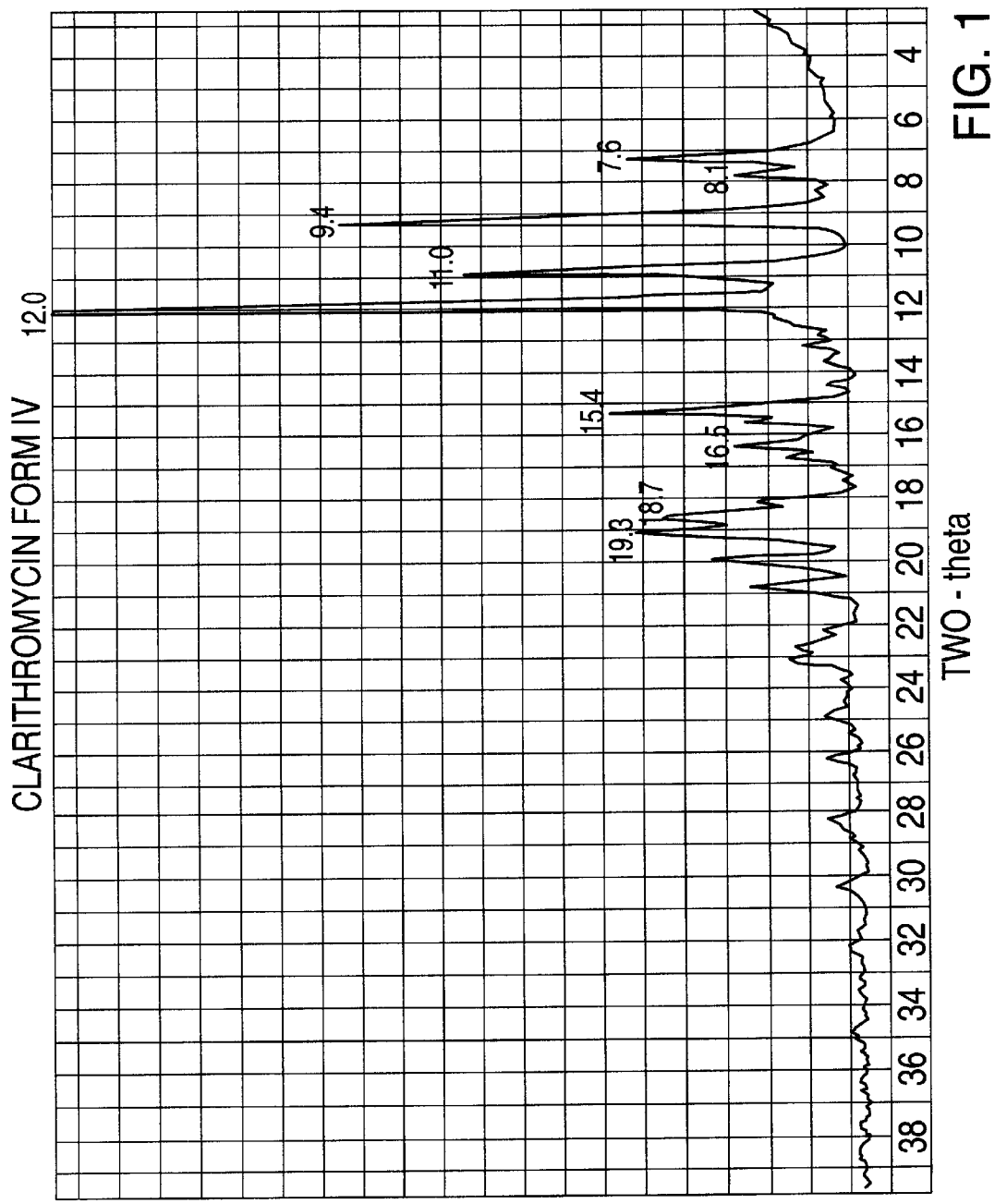
FIG. 1 shows the powder X-ray diffraction spectrum of clarithromycin 6-O-methylerythromycin A Form IV.

We have found that clarithromycin Form 0 undergoes transformation to Form II by simply slurrying the Form 0 clarithromycin with water. The present process for converting clarithromycin Form 0 to Form II is simpler and less expensive than previously described methods of converting Form 0 to Form II, which require for example, prolonged heating at high temperature.

Under different conditions, a novel polymorph of clarithromycin which we designate "Form IV" is formed. Our Form IV clarithromycin can be used as previously known forms of clarithromycin. It can be formulated into pharmaceutical compositions that include a therapeutically effective amount of clarithromycin Form IV and one or more pharmaceutically acceptable carriers. Those pharmaceutical compositions can be administered as a therapeutically effective antibiotic. Each of these aspects of the present invention is described in further detail below.

The terms "6-O-methylerythromycin A" and "clarithromycin" are used interchangeably herein and are meant to include clarithromycin in any crystalline form or mixtures thereof, as well as amorphous solids, syrups, or semisolids comprising 6-O-methylerythromycin A in any state of purity, unless specified otherwise, or as the context requires.

The term "Form 0" is used herein to mean the crystal Form 0 or Form 0 solvate of 6-O-methylerythromycin A. Form 0 solvate is characterized by 2-theta angle positions in the powder x-ray diffraction pattern of 4.6°±0.2, 6.50°±0.2, 7.6°±0.2, 9.2°±0.2, 10.2°±0.2, 11.0°±0.2, 11.6°±0.2, 12.5°±0.2, 13.8°±0.2, 14.8°±0.2, 17.0°±0.2, 18.2°±0.2, 18.9°±0.2 and 19.5°±0.2. This pattern may be somewhat varied depending on the solvent. For example a Form 0 ethanolate may be characterized by 2-theta angle positions of 4.7°±0.2, 6.6°±0.2, 7.7°±0.2, 9.3°±0.2, 10.4°±0.2, 11.1°±0.2, 11.9°±0.2, 12.7°±0.2, 13.9°±0.2, 15.0°±0.2, 17.2°±0.2, 18.5°±0.2, 19.1°±0.2, 19.7°±0.2, 23.1°±0.2 and 24.0°±0.2. The term "Form I" is used herein to mean the crystal Form I of clarithromycin. Form I has been characterized by 2-theta angle positions in the powder x-ray diffraction pattern of 5.2°±0.2, 6.7°±0.2, 10.2°±0.2, 12.3°±0.2, 14.2°±0.2, 15.4°±0.2, 15.7°±0.2, and 16.4°±0.2. Form I has also been characterized by an exothermic transition at 132.2° C. by differential scanning calorimetry, and by endothermic peaks at 223.4° C., and 283.3° C., followed by an exothermic peak at 306.9° C.

The term "Form II" is used herein to mean the crystal Form II of clarithromycin. Form II has been characterized by 2-theta angle positions in the powder x-ray diffraction pattern of 8.50°±0.2, 9.5°±0.2, 10.8°±0.2, 11.5°±0.2, 11.9°±0.2, 12.4°±0.2, 13.7°±0.2, 14.1°±0.2, 15.2°±0.2, 16.5°±0.2, 16.9°±0.2, 17.3°±0.2, 18.1°±0.2, 18.4°±0.2, 19.0°±0.2, 19.9°±0.2, and 20.5°±0.2. Form II has also been characterized by melting at 223.4° C., and by an endothermic peak at 283.3° C. by differential scanning calorimetry.

Formation of Clarithromycin Form II

The present invention relates to processes for converting clarithromycin Form 0 to clarithromycin Form II, which include slurrying clarithromycin Form 0 with water. The present invention also relates to a process of preparing clarithromycin Form II from erythromycin A, which includes slurrying clarithromycin Form 0 in water. In one embodiment, this method includes first converting erythromycin A to clarithromycin and thereafter slurrying clarithromycin Form 0 with water to form clarithromycin Form II. There are several methods by which clarithromycin may be formed from erythromycin A, as described further below. In certain of these methods, the initial form of clarithromycin that is formed is Form 0. In other methods, the initial form of clarithromycin that is formed is not Form 0, but rather another form that is subsequently converted to Form 0.

As used herein, the terms "slurrying" and "slurried" are intended to include stirring particles in a liquid, preferably water.

In the present invention, a wet solid of clarithromycin is obtained, for example by treating clarithromycin with ethanol, filtering and washing the precipitate with ethanol. The wet solid is slurried with water, preferably at ambient temperature, for about 1 hour. The slurrying step may include stirring the clarithromycin and water.

After clarithromycin Form 0 is converted to clarithromycin Form II by slurrying, the resulting crystalline clarithromycin Form II may then isolated, preferably by filtration and dried in an oven, preferably a vacuum oven, at a temperature of between about ambient temperature and about 70° C., preferably from about 40° C. to about 60° C., even more preferably, about 50° C. Preferably, the drying takes place under vacuum.

In the slurrying step of any of the embodiments that involve converting Form 0 to Form II described herein, clarithromycin Form 0 is slurried in about 2 to about 25 ml of water per gram of clarithromycin Form 0. More preferably clarithromycin Form 0 is slurried in about 3 to about 10 ml of water per gram of clarithromycin Form 0. Most preferably clarithromycin Form 0 is slurried in about 5 ml of water per gram of clarithromycin Form 0.

For purposes of this specification, ambient temperature is from about 20° C. to about 25° C.

The term "treating" as used herein refers to suspending, dissolving, washing, mixing, crystallizing or recrystallizing clarithromycin in any of the solvents described above.

As indicated above, processes for preparing clarithromycin Form II according to the present invention may include first converting erythromycin A to clarithromycin prior to slurrying the clarithromycin Form 0 with water to form clarithromycin Form II. This conversion of erythromycin A to clarithromycin may be performed by any method used by those in the art. In general, clarithromycin is prepared by methylation of the 6-hydroxy group of erythromycin A. However, in the conversion process it is necessary to protect various groups, especially hydroxy groups at positions of erythromycin A, which are potentially reactive with alkylating agents, prior to alkylation of the 6-hydroxy group. Examples of methods of preparing clarithromycin are described for example, in U.S. Pat. Nos. 4,331,803, 4,670,549, 4,672,109, 4,990,602, 5,858,986, 5,844,105 and 5,945,405, which are each herein incorporated by reference in there entirety. By way of example, U.S. Pat. Nos. 4,990,602 and 5,858,986 describe a method of preparing clarithromycin from erythromycin A by protecting the 9-oxo group with a substituted oxime group, protection of the C-2' and C-4" hydroxy groups, methylation of the C-6 hydroxy group, and deoximation and removal of the protecting groups. Various other methods of converting erythromycin A to clarithromycin that presently exist or methods that may be contemplated in the future may also be used.

Clarithromycin Form II Formed by Slurrying Form 0

The present invention also relates to clarithromycin Form II prepared by slurrying clarithromycin Form 0 in water, and pharmaceutical preparations including to clarithromycin Form II prepared by slurrying clarithromycin Form 0 in water.

Pharmaceutical compositions according to this embodiment include a therapeutically effective amount of clarithromycin Form II prepared by slurrying Form 0 in water or a pharmaceutically acceptable salt thereof and one or more pharmaceutically acceptable carriers. Such compositions may be administrated as set forth below with regard to compositions containing clarithromycin Form IV.

Clarithromycin Form IV

One aspect of the present invention provides a novel polymorph of clarithromycin designated as Form IV or a pharmaceutically acceptable salt thereof. This novel form of clarithromycin has a powder x-ray diffraction pattern with characteristic peaks at 7.6°±0.2, 8.10°±0.2, 9.4°±0.2, 11.0°±0.2, 12.0°±0.2, 15.4°±0.2, 16.50°±0.2, 18.7°±0.2, and 19.3°±0.2 degrees two-theta. FIG. 1 shows the x-ray diffraction pattern of a clarithromycin Form IV compound within the scope of the present invention.

Pharmaceutical Compositions Including Clarithromycin Form IV

Another aspect of the present invention provides pharmaceutical compositions that include a therapeutically effective amount of clarithromycin Form IV or a pharmaceutically acceptable salt thereof and one or more pharmaceutically acceptable carriers.

The term "clarithromycin Form IV" as used herein is meant to include clarithromycin Form IV as well as solids, syrups, or semisolids comprising clarithromycin Form IV in any state of purity, unless specified otherwise.

The pharmaceutical compositions of this invention are administered to humans and other animals by any acceptable route within sound medical judgment, such as orally, rectally, parenterally, intracisternally, intravaginally, intraperitoneally, topically (as by powders, ointments, or drops), bucally, or as an oral or nasal spray. Preferably, the pharmaceutical compositions of this invention are formulated for oral administration in solid or liquid form, for parenteral injection, or for rectal administration.

The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection include for example pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The pharmaceutical compositions of the present invention may also contain one or more adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include within the pharmaceutical composition one or more isotonic agents such as sugars, sodium chloride, and the like. Prolonged absorption of the injectable pharmaceutical form may be brought about by the inclusion of agents that delay absorption such as aluminum monostearate and gelatin.

In some cases, in order to prolong the effect of the clarithromycin Form IV, it is desirable to slow the absorption of the clarithromycin Form IV from subcutaneous or intramuscular injection. This may be accomplished for example by the use of a liquid suspension of crystalline or amorphous material with poor water solubility. The rate of absorption of the clarithromycin Form IV then depends upon its rate of dissolution which, in turn, may depend upon crystal size and crystalline form. Alternatively, delayed absorption of a parenterally administered clarithromycin Form IV form may be accomplished by dissolving or suspending the clarithromycin Form IV in an oil vehicle.

Injectable depot forms are made by forming microencapsule matrices of the clarithromycin Form IV in biodegradable polymers such as polylactide-polyglycolide. Depending upon the ratio of drug to polymer and the nature of the particular polymer employed, the rate of clarithromycin Form IV release can be controlled. Examples of other biodegradable polymers include poly(orthoesters) and poly(anhydrides). Depot injectable formulations are also prepared by entrapping the clarithromycin Form IV in liposomes or microemulsions that are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use.

Solid dosage forms for oral administration include capsules, tablets, pills, powders, and granules. In such solid dosage forms, the clarithromycin Form IV is mixed with at least one inert, pharmaceutically acceptable excipient or carrier such pharmaceutically acceptable excipients or carriers include sodium citrate or dicalcium phosphate and/or a) fillers or extenders such as starches, lactose, sucrose, glucose, mannitol, and silicic acid, b) binders such as, for example, carboxymethylcellulose, alginates; gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

Solid dosage forms of tablets, dragees, capsules, pills, and granules can be prepared with coatings and shells such as enteric coatings and other coatings well known in the pharmaceutical formulating art. They may optionally contain opacifying agents and can also be of a composition such that they release the clarithromycin Form IV only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more excipients, such as the above-mentioned excipients.

Liquid dosage form for oral administration include pharmaceutically acceptable emulsions, solutions, suspensions, syrups and elixirs. In addition to the clarithromycin Form IV, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Oral compositions according to the present invention may also include one or more adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the clarithromycin Form IV.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods of forming liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The clarithromycin Form IV is mixed under sterile conditions with a pharmaceutically acceptable carrier and any needed preservatives, buffers, or propellants, which may be required. Opthalmic formulations, eye ointments, powders and solutions are also contemplated as being within the scope of this invention.

Methods of Using Clarithromycin Form IV as a Therapeutic Agent

6-O-methylerythromycins are useful as anti-bacterial agents. Clarithromycin is especially effective in treatment of infections, particularly, by oral administration, and therefore it is a useful antibacterial agent.

Accordingly, one aspect of the present invention provides methods of using clarithromycin Form IV or a pharmaceutically acceptable salt as a therapeutic agent. Specifically, an embodiment of the present invention is a method of treating bacterial infections in a mammal in need of such treatment, which includes administering to the mammal a therapeutically effective amount of clarithromycin Form IV.

Actual dosage levels of clarithromycin Form IV in the pharmaceutical compositions of this invention may be varied so as to obtain an amount of the clarithromycin Form IV that is effective to achieve the desired therapeutic response for a particular patient, compositions, and mode of administration. The selected dosage level will depend on various factors such as the activity of the particular compound, the route of administration, the severity of the condition being treated, the size of the patient and the condition and prior medical history of the patient being treated. However, it is within the skill of the art to start doses of the clarithromycin Form IV at levels lower than required for to achieve the desired therapeutic effect and to gradually increase the dosage until the desired effect is achieved. Thus, an appropriate therapeutically effective amount may be determined by a doctor, veterinarian or other healthcare professional having experience in determining appropriate dosages for treatment.

Methods of Making Clarithromycin Form IV

Another embodiment of the present invention provides methods of making clarithromycin Form IV, which include converting erythromycin A to clarithromycin Form IV.

As described above, erythromycin A is converted to clarithromycin generally by methylation of the 6-hydroxy group of erythromycin A. In the conversion process it is necessary to protect various groups, especially the hydroxy groups at the 2' and 4" positions of erythromycin A. By way of example U.S. Pat. Nos. 4,990,602 and 5,858,986 describe a method of preparing clarithromycin from erythromycin A by oximation of the C-9 carbonyl, protection of the C-2' and C-4" hydroxy groups, methylation of the C-6 hydroxy group, and deoximation and removal of the protecting groups.

In the process of converting erythromycin A to clarithromycin Form IV, erythromycin A is first converted to an oxime form of erythromycin A that has protecting groups at the 2' and/or the 4" position, such as 6-O-methyl-2',4"-bis (trimethylsilyl)-erythromycin A 9-O-(2-methoxyprop-2-yl)

oxime. The oxime is produced by methods generally known in the art. 6-O-methyl-2',4"-bis(trimethylsilyl)-erythromycin A 9-O-(2-methoxyprop-2-yl)oxime is an example of an oxime form of erythromycin A that has a 2-methoxyprop-2-yl substituent on the oxime and silyl protecting groups at the 2' and 4" positions. The oxime may be substituted for example, with alkoxyalkyl groups other than 2-methoxyprop-2-yl, and the 2' and/or the 4" positions may be substituted for example, by protecting groups, such as silyl groups, other than trimethylsilyl. Examples of suitable protecting groups at the 2' and 4" positions include for example, trisubstituted silyl, acyl, alkylcarbonyl, alkoxycarbonyl, lower alkenyl monocarbonyl, lower alkoxycarbonyl, alkylcarbonyl or arylcarbonyl, or other groups known in the art, including those for example set forth in U.S. Pat. No. 5,837,829 The oxime may be protected by groups known in the art such as those set forth in U.S. Pat. Nos. 4,990,602 or 5,837,829, which are hereby incorporated by reference herein.

As indicated above, protecting groups protect the various positions from potentially reacting with alkylating agents during the alkylation of the 6-hydroxy group when the 6 position is methylated. Although the conversion from erythromycin A to the protected oxime, such as 6-O-methyl-2',4"-bis(trimethylsilyl)-erythromycin A 9-O-(2-methoxyprop-2-yl)oxime, may be accomplished by any methods known to those in the art, in a preferred method, erythromycin A is first oximated and subsequently protecting groups are added to the 2' and 4" positions.

Suitable methods for oximation and adding protecting groups are demonstrated in U.S. Pat. Nos. 5,858,986 and 4,990,602, which teach general methods of oximation that may be used in accordance with the present invention, such as by reacting erythromycin A with the substituted hydroxylamine $R^1ONH_2$, or by reacting erythromycin A with hydroxylamine hydrochloride in the presence of base, or hydroxylamine in the presence of acid, followed by reaction with $R^1X$, where $R^1$ is alkoxyalkyl. U.S. Pat. Nos. 5,858,986 and 4,990,602 further describe suitable methods for protecting the two hydroxy groups (i.e., at the 2' and 4" positions) with silyl groups. The hydroxy groups may be protected simultaneously or in different steps from one another.

Removal of the protecting groups and deoximation of 6-O-methyl-2',4"-bis(trimethylsilyl)-erythromycin A 9-O-(2-methoxyprop-2-yl)oxime (or other protected oxime) are then accomplished by treatment with acid and deoximating agent to give clarithromycin. Examples of suitable deoximating agents for use with the present invention include inorganic sulfur oxide compounds such as sodium hydrogen sulfite, sodium pyrosulfate, sodium thiosulfate, sodium sulfite, sodium hydrosulfite, sodium metabisulfite, sodium bisulfite, sodium dithionate, potassium hydrogen sulfite, potassium thiosulfate, potassium metabisulfite and the like. Particularly preferred deoximating agents are sodium metabisulfite and sodium bisulfite and the like. Deprotection may occur prior to deoximation or deprotection and deoximation may be accomplished in a single step ("one-pot" synthesis) by treatment with acid, such as formic acid, and deoximating agent.

The mixture of 6-O-methyl-2',4"-bis(trimethylsilyl)-erythromycin A 9-O-(2-methoxyprop-2-yl)oxime, acid, deoximating agent and aqueous solution, preferably aqueous ethanol, is stirred at reflux for an amount of time sufficient to essentially complete the reaction. The mixture is then cooled to about 0° C. and sodium hydroxide solution (at a concentration of about 20% to about 48%, preferably about 48%) is added at this temperature until the pH of the reaction mixture reaches greater than 8, preferably greater than 10, and most preferably about 10 to about 11. Crystalline clarithromycin is then isolated, preferably by filtration. The wet substance is then transferred to a reactor and water is added at about ambient temperature for about one hour while stirring. The solid is then filtered, washed with water and dried in an oven to give clarithromycin Form IV. The drying in an oven preferably takes place at a temperature of between ambient temperature and about 50° C., preferably from about 40° C. to about 50° C., even more preferably, about 50° C. Preferably, the drying takes place in a vacuum oven.

The following examples are provided to enable one skilled in the art to practice the invention and are merely illustrative of the invention. The examples should not be read as limiting the scope of the invention as defined in the claims.

EXAMPLE 1

Clarithromycin (5 g, assay~95%) was dissolved in 60 milliliters of ethanol at reflux. The solution was then cooled to about 10° C. and the precipitate was filtered and washed with 5 milliliters of cold ethanol. 6 grams of a wet solid were obtained, which powder x-ray diffraction analysis (PXRD) indicated was clarithromycin crystalline Form 0. The product so obtained was slurried with stirring in 25 milliliters of water at ambient temperature for about 1 hour and the solid substance was then filtered. Powder x-ray diffraction analysis was performed on the wet product and the product was determined to be polymorph II. The product was dried at temperature of about 50° C. under vacuum. The final product was 4.5 grams of pure clarithromycin (assay above 98%) polymorphic Form II.

EXAMPLE 2

To a mixture of 6-O-methyl-2',4"-bis(trimethylsilyl)-erythromycin A 9-O-(2-methoxyprop-2-yl)oxime (40 g), ethanol (120 ml), water (120 ml) and sodium metabisulfite (40.8 g), formic acid (2.8 ml) was added and the mixture was heated to reflux. Stirring at reflux was continued for 4 hours. Then the mixture was cooled to about 0° C. Sodium hydroxide solution (47%) was added at this temperature until the pH of the reaction mixture reached about 11. The precipitate that formed was filtered, washed twice with 160 ml water. The wet substance was transferred to a reactor and 4 volumes of water was added at room temperature and stirred for about 1 hour. The solid was filtered, washed with water (130 ml) and dried under vacuum at a temperature of 50° C. to give 26 grams of clarithromycin Form IV.

Example 2 shows one embodiment of the present invention, which includes a process for preparing 6-O-methylerythromycin A Form IV. It would be evident to those in the art based on this disclosure that similar processes may be employed in which different deoximating agents, acids, etc. are used and/or different amounts are used than those exemplified in the example, depending on factors such as availability of products or manufacturing or financial constraints, as long as the yielded product is 6-O-methylerythromycin A Form IV. Similarly, it would be apparent to one in the art that one may add steps to the above representative process, such as additional purification steps, as long as the yielded product is 6-O-methylerythromycin A Form IV.

Example 1 shows a particular embodiment of the present invention, which includes converting clarithromycin Form 0 to Form II by slurrying. It would be evident to those in the art based on the present disclosure that similar processes may be employed in which the process parameters are varied from those in the examples, for example if different amounts, temperatures, isolation techniques, etc. are employed, as long as the yielded product is clarithromycin Form II.

The present invention provides methods for converting clarithromycin Form 0 to clarithromycin Form II by slurrying in water, pharmaceutical compositions including clarithromycin Form II prepared by slurrying Form 0, clarithromycin Form IV, pharmaceutical compositions including clarithromycin Form IV, methods of treatment using clarithromycin Form IV, and processes for preparing clarithromycin Form IV. Although the present invention has been described with respect to certain exemplary embodiments, there are many other variations of the above-described embodiments, which will be apparent to those skilled in the art, even where elements or steps have not explicitly been designated as exemplary. It is understood that these modifications are within the teaching of the present invention.

We claim:

1. A process for converting clarithromycin Form 0 to clarithromycin Form II comprising the steps of:
    a) slurrying clarithromycin Form 0 in water to form clarithromycin Form II; and
    b) separating the clarithromycin Form II.

2. The process of claim 1, wherein the clarithromycin Form 0 is slurried in about 2 to about 25 ml of water per gram of clarithromycin Form 0.

3. The process of claim 1, wherein the clarithromycin Form 0 is slurried in about 3 to about 10 ml of water per gram of clarithromycin Form 0.

4. The process of claim 1, wherein the slurrying takes place at about ambient temperature.

5. The process of claim 1, further comprising drying the clarithromycin Form II that results from slurrying the clarithromycin Form 0 with water.

6. The process of claim 5, wherein the drying takes place under vacuum.

7. A process for preparing clarithromycin Form II comprising the steps of:
    a) converting erythromycin A to clarithromycin Form 0;
    b) slurrying the clarithromycin Form 0 in water to form clarithromycin Form II; and
    c) separating the clarithromycin Form II.

8. The process of claim 7, wherein the clarithromycin Form 0 is slurried in about 2 to about 25 ml of water per gram of clarithromycin Form 0.

9. The process of claim 7, wherein the clarithromycin Form 0 is slurried in about 3 to about 10 ml of water per gram of clarithromycin Form 0.

10. The process of claim 7, wherein the slurrying takes place at about ambient temperature.

11. The process of claim 7, further comprising drying the clarithromycin Form II that results from slurrying the clarithromycin Form 0 with water.

12. The process of claim 11, wherein the drying takes place under vacuum.

13. Clarithromycin Form IV, characterized by peaks in the powder x-ray diffraction at values of two theta of 7.6°±0.2, 8.1°±0.2, 9.4°±0.2, 11.0°±0.2, 12.0°±0.2, 15.4°±0.2, 16.5°±0.2, 18.7°±0.2, and 19.3°±0.2.

14. A pharmaceutical composition comprising a therapeutically effective amount of clarithromycin Form IV according to claim 13 and at least one pharmaceutically acceptable carrier.

15. The pharmaceutical composition of claim 14, wherein the composition is in a powder form.

16. The pharmaceutical composition of claim 14, wherein the composition is in a suspension form.

17. The pharmaceutical composition of claim 14, wherein the composition is in an ointment form.

18. A method of treating bacterial infections in a mammal in need of such treatment comprising administering to the mammal a therapeutically effective amount of clarithromycin Form IV according to claim 13.

19. The method of claim 18, wherein the clarithromycin Form IV is administered to said mammal by a method selected from the group consisting of oral, rectal, parenteral, intracisternal, intravaginal, intraperitoneal, topical, bucal, and nasal.

20. A process for preparing clarithromycin Form IV comprising
    converting erythromycin A to a 6-O-methyl erythromycin A oxime having one or more oxime protecting groups and protecting groups at the 2' and 4" positions;
    mixing the a 6-O-methyl erythromycin A oxime with aqueous ethanol, a deoximating agent and formic acid and stirring at reflux for an amount of time sufficient to complete a reaction;
    cooling the mixture to about 0° C.; and
    adding sodium hydroxide solution until the pH reaches about 10 to about 11.

21. The process of claim 20, wherein the deoximating agent is sodium metabisulfite.

22. The process of claim 20, further comprising isolating crystalline clarithromycin after adding sodium hydroxide solution.

23. The process of claim 22, further comprising filtering and washing said clarithromycin.

24. The process of claim 23, further comprising drying said clarithromycin to yield clarithromycin Form IV.

25. A process for preparing clarithromycin Form IV comprising
    (a) converting erythromycin A to an oxime of erythromycin A, which has a protecting group on the oxime and a protecting group on one or both of the 2' and 4" positions,
    (b) mixing the oxime with aqueous ethanol, a deoximating agent and formic acid,
    (c) heating the mixture formed in step (b) at reflux temperature,
    (d) cooling the mixture of step (c) to about 0° C.,
    (e) adding sodium hydroxide solution to the mixture of step (d) until the pH of the mixture reaches about 10 to about 11,
    (f) isolating crystalline clarithromycin from the mixture of step (e),
    (g) transferring the clarithromycin of step (f) to a reactor and treating the mixture with water at about ambient temperature,
    (h) filtering and washing the clarithromycin of step (g), and
    (i) drying the clarithromycin of step (h) to yield clarithromycin Form IV.

26. The process of claim 25, wherein the deoximating agent is sodium metabisulfite.

27. The process of claim 25, wherein the drying of step (i) takes place at a temperature from about ambient temperature to about 50°.

28. The process of claim 25, wherein the drying of step (i) takes place in a vacuum oven.

29. A process for preparing clarithromycin Form IV comprising
- (a) converting erythromycin A to 6-O-methyl-2',4"-bis(trimethylsilyl)-erythromycin A 9-O-(2-methoxyprop-2-yl)oxime,
- (b) mixing the 6-O-methyl-2',4"-bis(trimethylsilyl)-erythromycin A 9-O-(2-methoxyprop-2-yl)oxime with aqueous ethanol, a deoximating agent and formic acid,
- (c) heating the mixture formed in step (b) at reflux temperature,
- (d) cooling the mixture of step (c) to about 0° C.,
- (e) adding sodium hydroxide solution to the mixture of step (d) until the pH of the mixture reaches about 10 to about 11,
- (f) isolating crystalline clarithromycin from the mixture of step (e),
- (g) transferring the clarithromycin of step (f) to a reactor and treating the mixture with water at about ambient temperature,
- (h) filtering and washing the clarithromycin of step (g), and
- (i) drying the clarithromycin of step (h) to yield clarithromycin Form IV.

30. The process of claim 29, wherein the deoximating agent is sodium metabisulfite.

31. The process of claim 29, wherein the drying of step (i) takes place at a temperature from about ambient temperature to about 50°.

32. The process of claim 29, wherein the drying of step (i) takes place in a vacuum oven.

33. A process for preparing clarithromycin Form IV comprising
- converting erythromycin A to a 6-O-methyl erythromycin A oxime having one or more oxime protecting groups and protecting groups at the 2' and 4" positions;
- mixing the a 6-O-methyl erythromycin A oxime with aqueous solution, a deoximating agent and formic acid and stirring at reflux for an amount of time sufficient to complete a reaction;
- cooling the mixture to about 0° C.; and
- increasing the pH to greater than 8.

34. The process of claim 33, wherein the deoximating agent is sodium metabisulfite.

35. The process of claim 33, wherein the aqueous solution is preferably aqueous ethanol.

36. The process of claim 33 or 35, wherein pH is increased to greater than 10.

37. The process of claim 33 or 35, wherein pH is increased to between about 10 and about 11.

38. The process of claim 33, further comprising isolating crystalline clarithromycin after adding sodium hydroxide solution.

39. The process of claim 38, further comprising filtering and washing said clarithromycin.

40. The process of claim 39, further comprising drying said clarithromycin to yield clarithromycin Form IV.

* * * * *